(12) United States Patent
Hang

(10) Patent No.: US 12,377,207 B2
(45) Date of Patent: Aug. 5, 2025

(54) TRANSPORTATION TRAY FOR TRANSPORTATION OF A FILLED SYRINGE

(71) Applicant: Becton, Dickinson and Company, Franklin Lakes, NJ (US)

(72) Inventor: Tianqi Hang, Cliffside Park, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 97 days.

(21) Appl. No.: 18/271,811

(22) PCT Filed: Jan. 12, 2022

(86) PCT No.: PCT/US2022/012150
§ 371 (c)(1),
(2) Date: Jul. 11, 2023

(87) PCT Pub. No.: WO2022/155224
PCT Pub. Date: Jul. 21, 2022

(65) Prior Publication Data
US 2024/0066204 A1 Feb. 29, 2024

Related U.S. Application Data

(60) Provisional application No. 63/136,673, filed on Jan. 13, 2021.

(51) Int. Cl.
*A61M 5/00* (2006.01)
*B65D 25/10* (2006.01)
*B65D 43/02* (2006.01)
*B65D 43/16* (2006.01)

(52) U.S. Cl.
CPC .......... *A61M 5/008* (2013.01); *B65D 25/105* (2013.01); *B65D 43/0202* (2013.01); *B65D 43/16* (2013.01); *A61M 5/001* (2013.01); *B65D 2251/0003* (2013.01); *B65D 2313/04* (2013.01)

(58) Field of Classification Search
CPC .. A61B 5/33; A61B 5/30; A61B 5/001; A61B 5/008; B65D 1/36; A61J 7/0069
See application file for complete search history.

(56) References Cited

U.S. PATENT DOCUMENTS

| | | | | |
|---|---|---|---|---|
| 2,955,705 A | * | 10/1960 | Krueger, Sr. | ......... A61M 5/002 220/377 |
| 3,853,158 A | * | 12/1974 | Whitty | ................ A61M 5/1782 141/330 |
| 3,961,721 A | * | 6/1976 | Gordon | ................ B65D 43/169 220/837 |
| 4,015,709 A | * | 4/1977 | Millet | ................ B65D 77/2064 206/521 |

(Continued)

FOREIGN PATENT DOCUMENTS

| | | | |
|---|---|---|---|
| EP | 790063 A1 * | 8/1997 | ............ A61M 5/002 |
| WO | WO2007130809 A2 | 11/2007 | |
| WO | WO2020195354 A1 | 10/2020 | |

*Primary Examiner* — Mollie Impink
(74) *Attorney, Agent, or Firm* — Dickinson Wright PLLC

(57) ABSTRACT

A transportation tray to transport filled syringes, the tray including a front shelf spaced apart from a rear shelf, with the front shelf and the rear shelf being on approximately the same plane. The front shelf includes at least one set of paired flexible fingers, the paired flexible fingers being spaced apart sufficiently to accommodate a barrel of a syringe and to thus hold the syringe on the tray.

18 Claims, 9 Drawing Sheets

(56) References Cited

U.S. PATENT DOCUMENTS

| | | | | |
|---|---|---|---|---|
| 5,892,233 | A * | 4/1999 | Clement | A61L 2/10 |
| | | | | 250/455.11 |
| 9,839,236 | B2 * | 12/2017 | Liu | A24F 40/95 |
| 9,987,383 | B2 * | 6/2018 | Bilenko | A61L 2/10 |
| 11,779,424 | B2 * | 10/2023 | Voltti | A61C 19/02 |
| | | | | 206/368 |
| 2005/0256453 | A1 * | 11/2005 | Nagamatsu | A61M 25/1018 |
| | | | | 141/2 |

* cited by examiner

TRANSPORTATION TRAY FOR TRANSPORTATION OF A FILLED SYRINGE

FIELD OF THE INVENTION

This present disclosure relates generally to an apparatus and method for transportation of medicaments, and more particularly to a transportation tray for transportation of filled syringes of medicaments.

BACKGROUND OF THE INVENTION

This section provides background information which is not necessarily prior art to the inventive concepts associated with the present disclosure.

In a hospital setting it was common practice for a nurse or doctor to administer medicaments, such as insulin, at the bedside using a multiuse vial of the medicament. This practice was rapid and did not involve any possibility for loss of the medicament from the syringe between the time of withdrawal from the vial and administration to the patient. In recent years the practice has been altered. Currently, a more common practice is for the hospital pharmacy to prepare the medicament and to load it into a syringe, which a doctor or nurse then has to get from the pharmacy. The loaded syringe then needs to be transported from the pharmacy to the patient prior to administration. Often these syringes are carried by hand or clipped to a patient chart. Many times this results in some loss of the medicament during the transportation process. The syringe plunger may be accidently bumped or moved during transport and medicament may be lost or air may be introduced into the syringe. The loose syringe can also be dropped or contaminated by exposure to the environment during transport. In addition, to increase efficiency often times a nurse or doctor will retrieve multiple syringes for multiple patients at one time, thus there is a possibility of getting the syringes mixed up and delivering an incorrect dosage or medicament to a patient.

Thus, it is desirable to provide a safe and effective way to transport one or more filled syringes from a first location to a second location without loss of any medicament from the syringe, without the possibility of mixing up the syringes and without the possibility of cross-contamination.

SUMMARY OF EMBODIMENTS OF THE INVENTION

This section provides a general summary of the present disclosure and is not intended to be interpreted as a comprehensive disclosure of its full scope or all features, aspects and objectives.

One or more aspects of the present invention are achieved by providing a transportation tray to transport filled syringes, the tray including a front shelf spaced apart from a rear shelf, with the front shelf and the rear shelf being on approximately the same plane. The front shelf includes at least one set of paired flexible fingers, the paired flexible fingers being spaced apart sufficiently to accommodate a barrel of a syringe and to thus hold the syringe on the tray.

These and other features and advantages of this disclosure will become more apparent to those skilled in the art from the detailed description herein. The drawings that accompany the detailed description are described below.

BRIEF DESCRIPTION OF THE DRAWINGS

The drawings described herein are for illustrative purposes only of selected aspects and not all implementations, and are not intended to limit the present disclosure to only that actually shown. With this in mind, various features and advantages of example aspects of the present disclosure will become apparent to one possessing ordinary skill in the art from the following written description and appended claims when considered in combination with the appended drawings, in which:

DETAILED DESCRIPTION OF EMBODIMENTS OF THE PRESENT INVENTION

Figure 1:
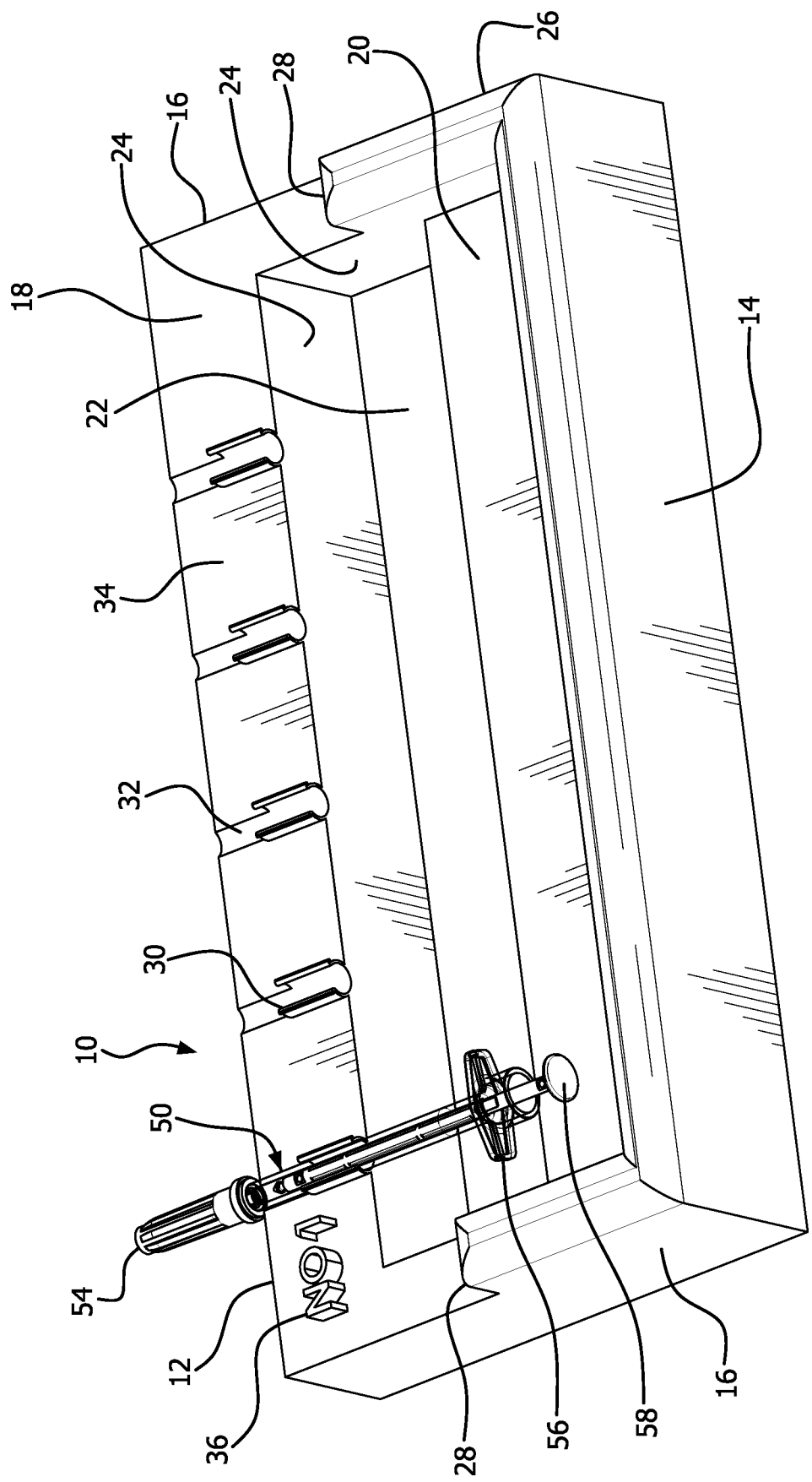
FIG. 1 is a top perspective view of a transportation tray for a plurality of loaded syringes according to one embodiment of the present invention.

In the following description, details are set forth to provide an understanding of the present disclosure.

The embodiments are not intended to be mutually exclusive so that the features of one embodiment can be combined with other embodiments as long as they do not contradict each other.

For clarity purposes, example aspects are discussed herein to convey the scope of the disclosure to those skilled in the relevant art. Numerous specific details are set forth such as examples of specific components, devices, and methods, to provide a thorough understanding of various aspects of the present disclosure. It will be apparent to those skilled in the art that specific details need not be discussed herein, such as well-known processes, well-known device structures, and well-known technologies, as they are already well understood by those skilled in the art, and that example embodiments may be embodied in many different forms and that neither should be construed to limit the scope of the disclosure.

The terminology used herein is for the purpose of describing particular example aspects only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. Method steps, processes, and operations described herein are not to be construed as necessarily requiring their performance in the particular order discussed or illustrated, unless specifically identified as an order of performance. It is also to be understood that additional or alternative steps may be employed.

When an element or feature is referred to as being "on," "engaged to," "connected to," "coupled to" "operably connected to" or "in operable communication with" another element or feature, it may be directly on, engaged, connected or coupled to the other element or layer, or intervening elements or features may be present. In contrast, when an element is referred to as being "directly on," "directly engaged to," "directly connected to," or "directly coupled to" another element or feature, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly and expressly indicated by the context. Thus, a first element, component, region, layer or section discussed below could be termed a second element, component, region, layer or section without departing from the teachings of the example embodiments.

For purposes of description herein, the terms "upper," "lower," "right," "left," "rear," "front," "vertical," "horizontal," and derivatives thereof shall relate to the invention as oriented in the FIGS. However, it is to be understood that the present disclosure may assume various alternative orientations and step sequences, except where expressly specified to the contrary. It is also to be understood that the specific devices and processes illustrated in the attached drawings, and described in the following specification are exemplary aspects of the inventive concepts defined in the appended claims. Hence, specific dimensions and other physical characteristics relating to the aspects disclosed herein are not to be considered as limiting, unless the claims expressly state otherwise. Terms of degree, such as "substantially" or "approximately," are understood by those skilled in the art to refer to reasonable ranges around and including the given value and ranges outside the given value, for example, general tolerances associated with manufacturing, assembly, and use of the embodiments. The term "substantially," when referring to a structure or characteristic, includes the characteristic that is mostly or entirely present in the characteristic or structure.

Referring in more detail to the drawings, FIG. 1 is a top perspective view of a transportation tray for a plurality of loaded syringes according to one embodiment of the present invention. The transportation tray is shown generally at 10 with a single syringe 50 loaded into the tray 10. The syringe 50 includes finger supports 56 and a plunger 58 as known to one of skill in the art. The tray 10 includes a front sidewall 12 an opposed rear sidewall 14 and a pair of opposing end walls 16. The tray 10 is shown as having a generally rectangular shape although other shapes may be utilized as would be understood by one of skill in the art. The tray 10 further includes a front shelf 18 and a rear shelf 20; preferably, the front shelf 18 and the rear shelf 20 are substantially of the same height and on substantially the same plane. The distance between the front shelf 18 and the rear shelf 20 is sized such that when the syringe 50 is loaded in the tray 10 the rear portion of the syringe 50 is supported on the rear shelf 20. Located between the front shelf 18 and the rear shelf 20 is a central hole 22 defined by four interior walls 24.

The central hole 22 is shown as having a rectangular shape, however, as known by one of skill in the art other shapes could be used. The central open space 22 allows a user to hold the tray 10 in multiple ways by gripping the tray 10 between the front sidewall 12 and one of the interior walls 24. A three-sided raised wall 26 is positioned on top of the two end walls 16 and the rear sidewall 14. The raised wall 26 is adjacent to and extends above the rear shelf 20. The raised wall 26 includes a pair of end surfaces 28. The front shelf 18 includes a plurality of sets of paired flexible fingers 30 and a groove 32 located between each of the paired flexible fingers 30, the sets of paired flexible fingers 30 are spaced apart from each other. In addition, located between each set of paired flexible fingers 30 is an open space 34. The front shelf 18 further includes optional indicia 36 to serve as an identifying mark to identify each tray 10. The indicia 36 can use any characters to provide a method of identifying one tray 10 from another. The open spaces 34 serve as a location where a label can be placed to identify the contents of a syringe 50 located in an adjacent set of paired flexible fingers 30 to ensure that the medicament is given to the correct patient and to identify the contents of the syringe 50.

Figure 2:
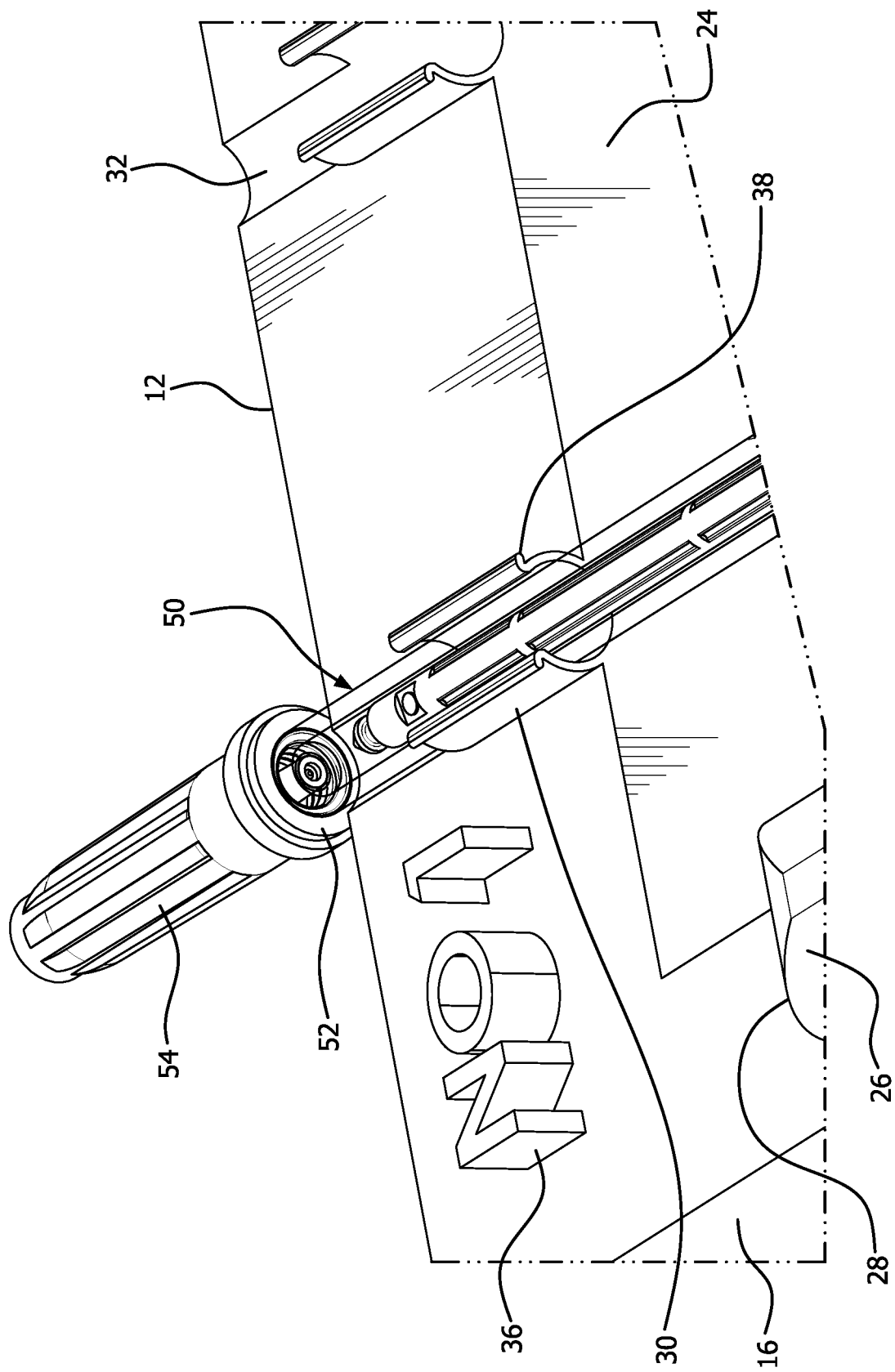
FIG. 2 is a close up view of a syringe secured in the transportation tray of FIG. 1.

FIG. 2 is a close up view of a syringe 50 secured between a pair of flexible fingers 30 in the transportation tray 10. The flexible fingers 30 are spaced apart a sufficient distance to accommodate a barrel of a syringe 50 between them. As shown each flexible finger 30 is formed on the front shelf 18 and each has a back bent or bent back edge 38. With the back bent edges 38, it easier to insert a syringe 50 between the flexible fingers 30. As shown, the syringe 50 includes a syringe hub 52 and a needle cover 54. The syringe 50 is preferably positioned in the tray 10 such that the syringe hub 52 is located against the front sidewall 12 when secured in the paired flexible fingers 30. In a preferred embodiment the entire tray 10 including the paired flexible fingers 30 and grooves 32 are formed as a unitary piece.

The tray 10 can be created with flexible fingers 30 and grooves 32 designed to accommodate any sized syringe 50. For insulin syringes, the typical sizes are 0.3 milliliter, 0.5 milliliter and 1 milliliter syringes. Preferably, the paired flexible fingers 30 have a sufficient amount of flex to accommodate any one of these three sizes all with the same size flexible fingers 30. If it is desirable to accommodate larger syringes the flexible fingers 30 and groove 32 can be formed larger and spaced further apart to accommodate any sized syringes without departing form the present invention's scope. In addition, a tray 10 can be designed to have paired flexible fingers 30 and groves 32 of different sizes such that the same tray 10 can accommodate a variety of sized syringes 50. The tray 10 is dimensioned such that the finger supports 56 and plunger 58 of a syringe 50 located in a pair of flexible fingers 30 is supported on the rear shelf 20. The rear shelf 20 is deep enough to accommodate the finger supports 56 and plunger 58 even when the plunger 58 is fully pulled out to completely fill the syringe 50 with a medicament. The raised wall 26 extends above the rear shelf 20 sufficiently high enough that it is higher than the height of the finger supports 56 and plunger 58 when they are located on the rear shelf 20. Thus a filled syringe 50 located in a set of paired flexible fingers 30 is fully protected and the plunger 58 cannot be disrupted during transportation of the syringe 50 in the tray 10. The size of the central hole 22 can be made larger to accommodate syringes 50 having a longer length and the raised wall 26 can be made higher without departing form the present invention's scope, as would be known to one of skill in the art.

Figure 3:
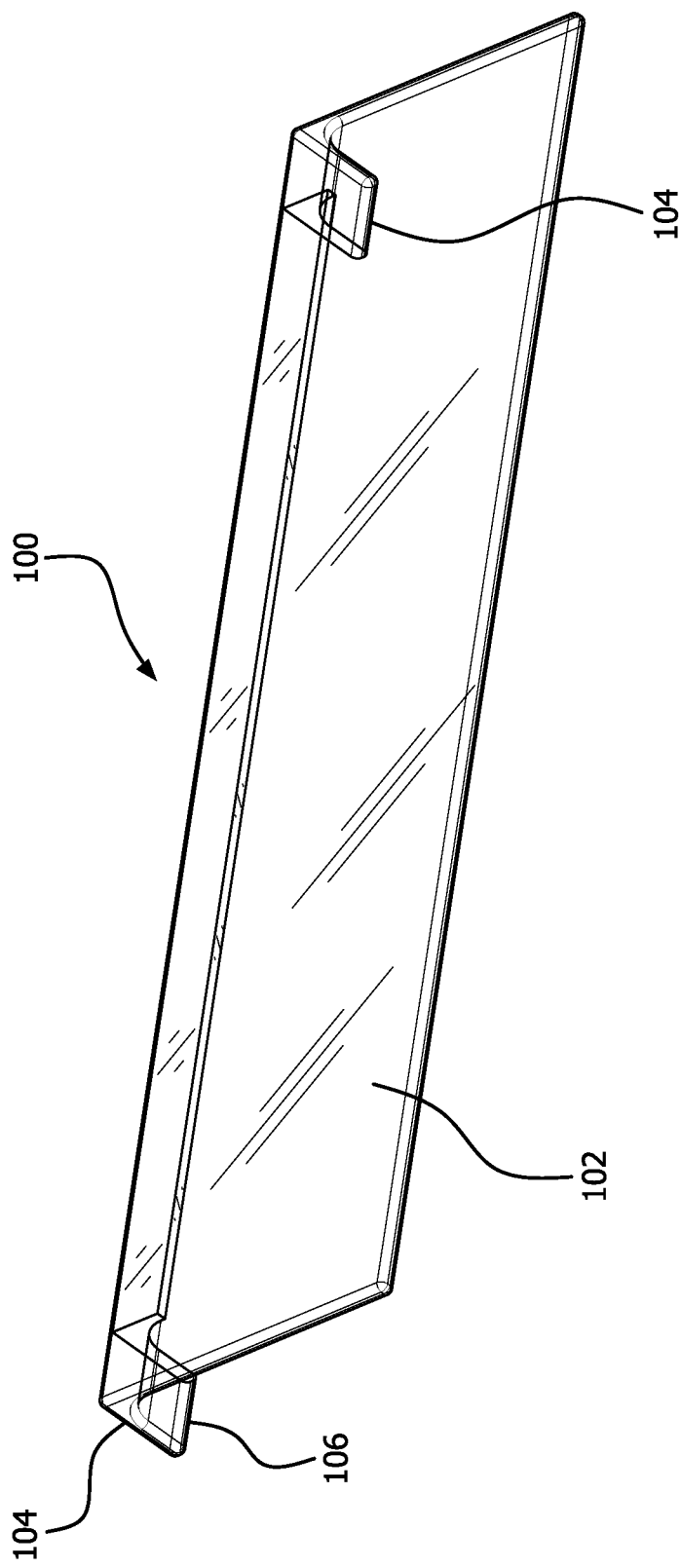
FIG. 3 is a top perspective view of an optional transportation tray cover according to the present invention.
Figure 4:
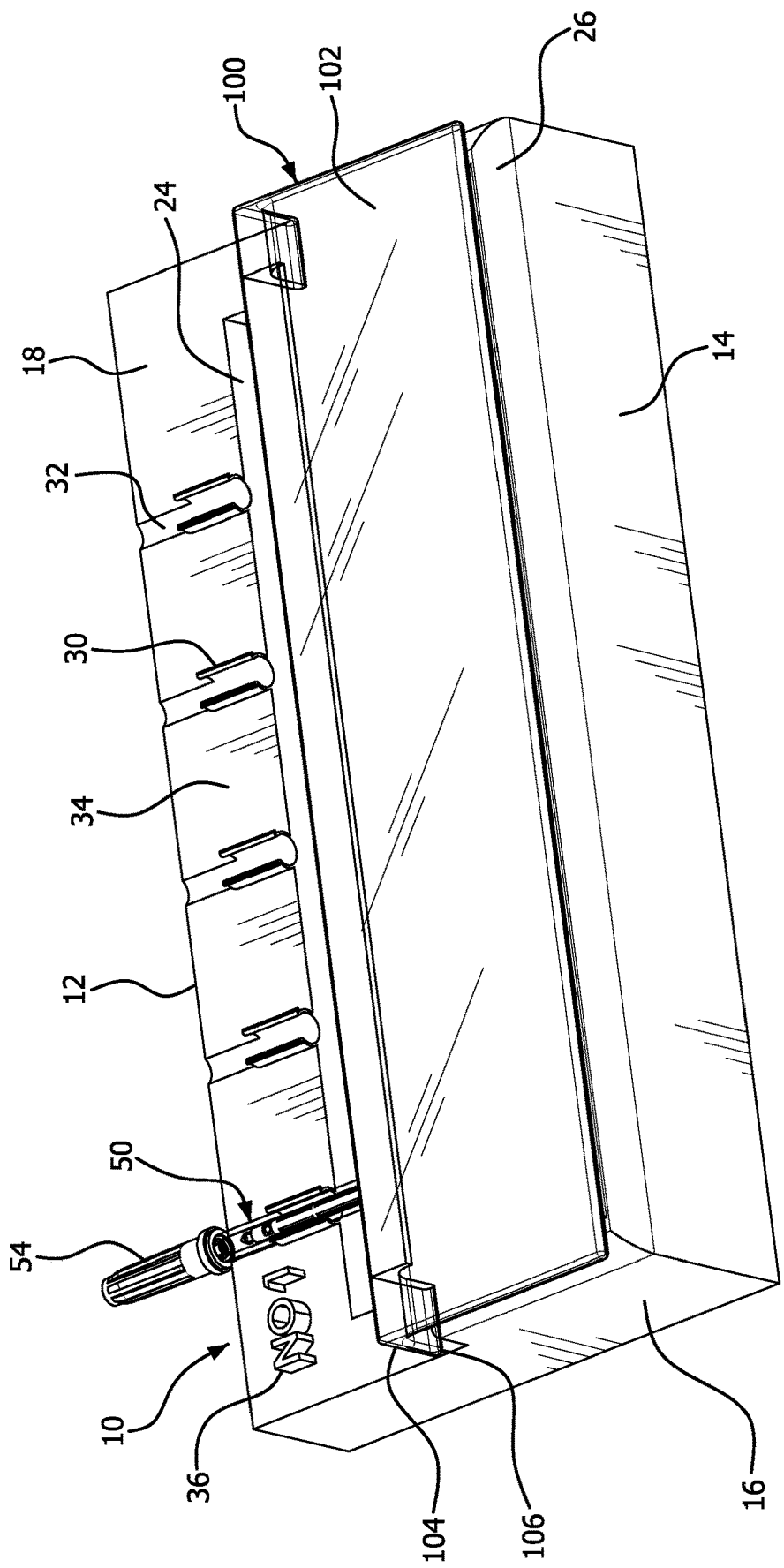
FIG. 4 is a top perspective view of the transportation tray of FIG. 1 with the optional cover of FIG. 3 in place.

FIG. 3 is a top perspective view of an optional transportation tray cover shown generally at 100 according to the present invention. The tray cover 100 includes a planar surface 102 and extending below the planar surface 102, a pair of tabs 104. According to one embodiment, the tabs 104 are preferably positioned at approximately 90 degrees relative to the planar surface 102. The cover 100 is dimensioned to fit on top of the raised wall 26 with the tabs 104 located against the end surfaces 28 as shown in FIG. 4. The tray cover 100 in FIG. 4 is shown as opaque, meaning one cannot see through it; however, as noted above, the tray cover 100 can also be transparent. Preferably, one of either the tabs 104 or the end surfaces 28 includes magnetic pads 106 and the other includes metal pads such that when brought in close contact the cover 100 is magnetically secured to the tray 10 in a removable manner by this magnetic interface. Other methods of securing the cover 100 to the tray 10 in a removable manner can include use of snap tabs on the end surfaces 28 or slots in the tray 10 adjacent the end surfaces 28 to accommodate the tabs 104 as would be known by one of skill in the art. Preferably the cover 100 is formed of a transparent material so the syringe 50 is visible thorough it. The cover 100 can also be made to be opaque or of one or more solid colors. The cover 100, when in place, further ensures the syringe 50 cannot be disturbed during transport of the tray 10.

Figure 5:
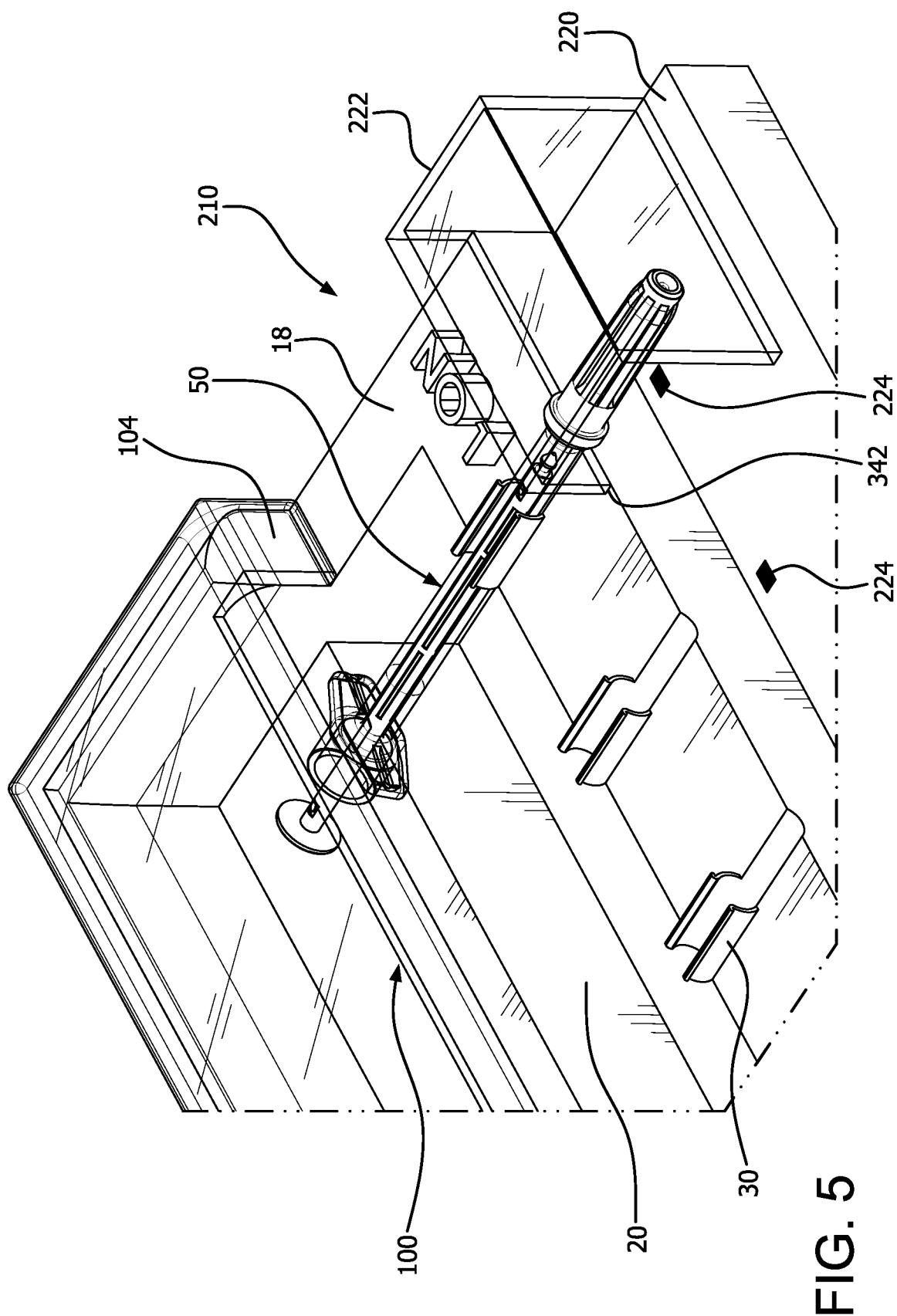
FIG. 5 is a partial top view of another embodiment of a transportation tray according to the present invention.

In FIG. 5, another embodiment of a transportation tray is shown generally at 210. The common features between this tray 210 and the one shown in FIGS. 1-4 are labeled with the same reference numbers. The additional features of this tray 210 include a third shelf 220 located adjacent to the front shelf 18. The third shelf 220 accommodates at least one cover 222 and is preferably lower in height than the front shelf 18. In a hospital pharmacy setting a user has to remove the needle cover 54 from the syringe 50 to fill it with the medicament. Then the needle cover 54 is replaced to ensure sterility. But this process can lead to unintentional needle sticks. To avoid this possibility, embodiments of the present invention include the use of a cover 222, preferably one cover 222 for each set of paired flexible fingers 30. In use, the pharmacy fills the syringe 50 with the medicament, places it in the tray 210 and then puts the cover 222 over the needle without need to replace the needle cover 54. The pharmacy fills all of the required syringes 50 and uses a cover 222 to cover each syringe's bare needle. Although the needle cover 54 is shown in FIG. 5, it does not have to be replaced on the syringe 50.

According to one embodiment, to secure the cover 222 in place during transport, preferably there is a magnetic interface 324 between the cover 222 and the tray 210, preferably on the front shelf 18. Alternatively, the magnetic interface can be located between the cover 222 and the third shelf 220. This magnetic interface 324 means one of the front shelf 18 or the cover 222 is magnetic and the other includes a metal portion to ensure a magnetic connection when they are brought into proximity to each other. Likewise, the magnetic interface 324 on the third shelf 220 includes one of the cover 222 or the third shelf 220 being magnetic and the other including a metal portion to ensure a magnetic connection when they are brought into proximity with each other. An additional feature of the tray 210 is the inclusion of an ultraviolet (UV) light source 224 located in the area covered by the cover 222. This UV light source 224 has sufficient power to ensure sterility of the exposed needle and the entire area under the cover 222. The light source 224 would be activated by a switch on the tray 210 or other means for a period of time, such as 30 seconds, to ensure sterility of everything covered by the cover 222.

Figure 6:
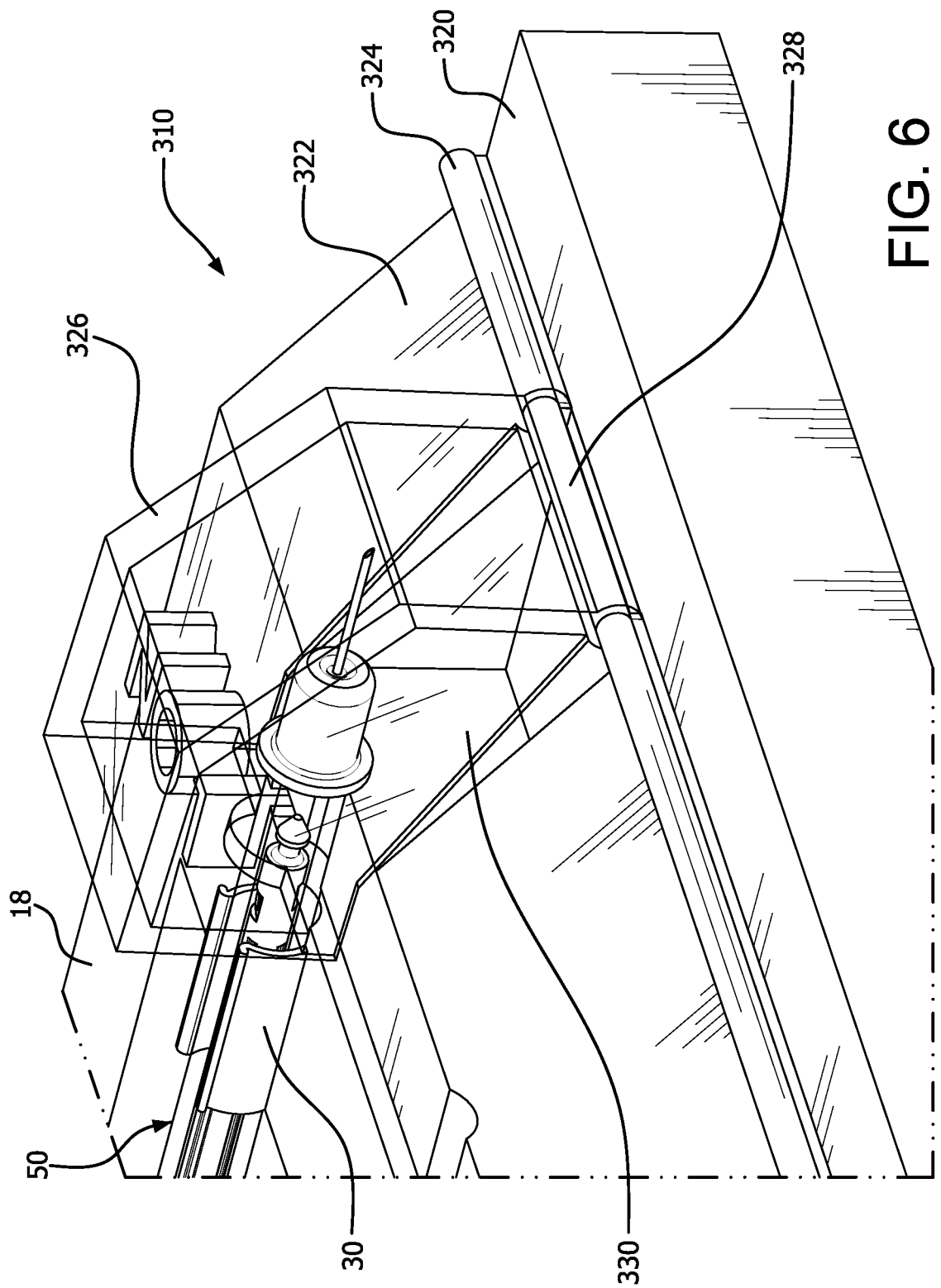
FIG. 6 is a partial view of another embodiment of a transportation tray according to the present invention.

FIG. 6 is a partial view of another embodiment of a transportation tray according to the present invention shown generally at 310. The common features between this tray 310 and the one shown in FIGS. 1-4 are labeled with the same reference numbers. The transportation tray 310 includes a third shelf 320 joined to the front shelf 18 by a ramp 322. The third shelf 320 is lower in height than the front shelf 18. A hinge pin 324 runs the length of the tray 310 where the ramp 322 meets the third shelf 320. Although shown as a continuous length, the hinge pin 324 could be segmented without departing form the present invention's scope, as would be known to one of skill in the art.

A hinged cover 326 having a hinge 328 that is received on the hinge pin 324 is shown. The hinged cover 326 fits over an exposed needle of a syringe 50 loaded into the tray 310, thus, preferably, there are as many hinged covers 326 as there are paired flexible fingers 30 on the tray 310. According to one embodiment, the ramp 322 includes a plurality of recesses 330 located in line with each of the paired flexible finger 30 as shown. The hinged cover 326 covers the area from the hinge pin 324 to the front shelf 18 including the recess 330. This configuration also ensures that after the pharmacy has filled the syringe 50, it can be loaded into the tray 310 without having to replace the needle cover 54 and thus avoiding the possibility of an accidental needle stick.

Figure 7:
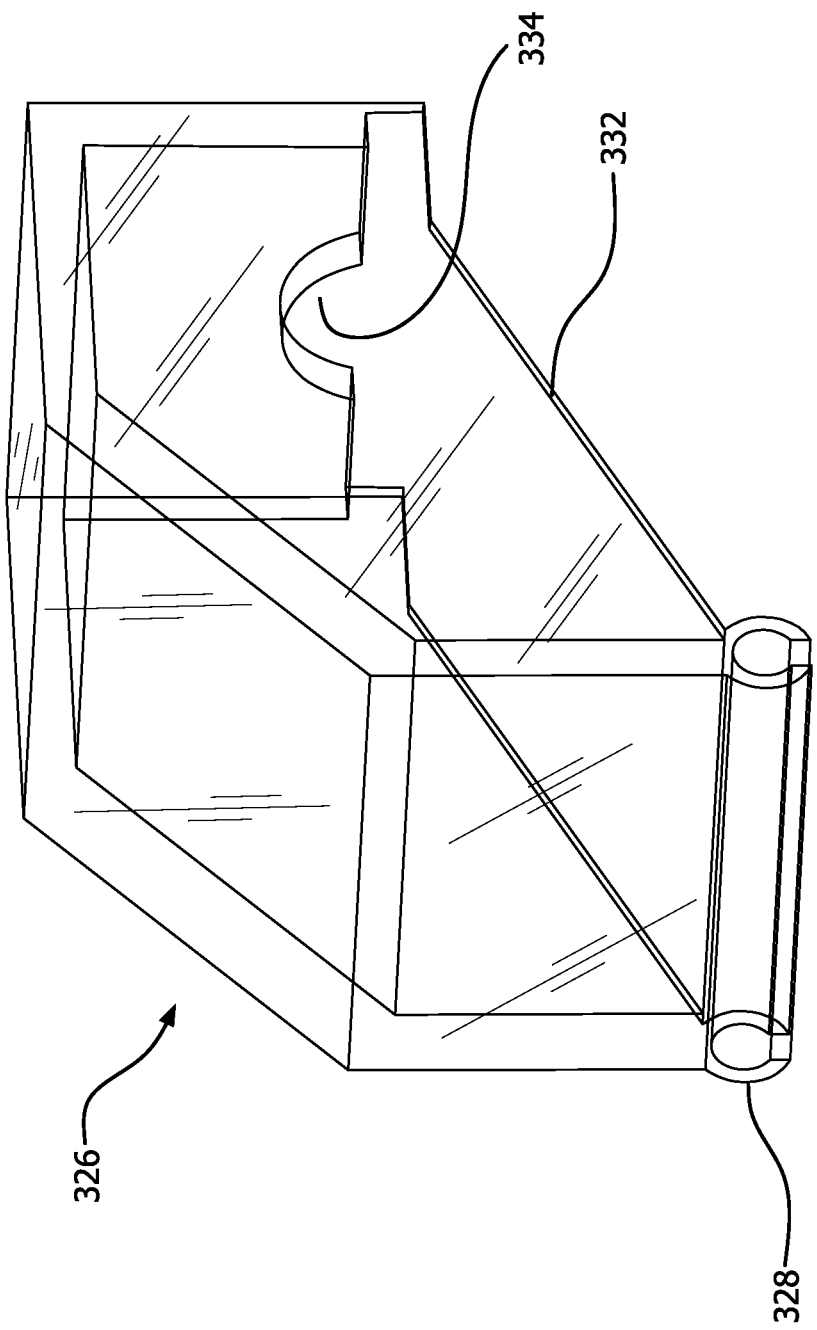
FIG. 7 is a detailed view of a hinged cover as shown in FIG. 6 according to the present invention.
Figure 8:
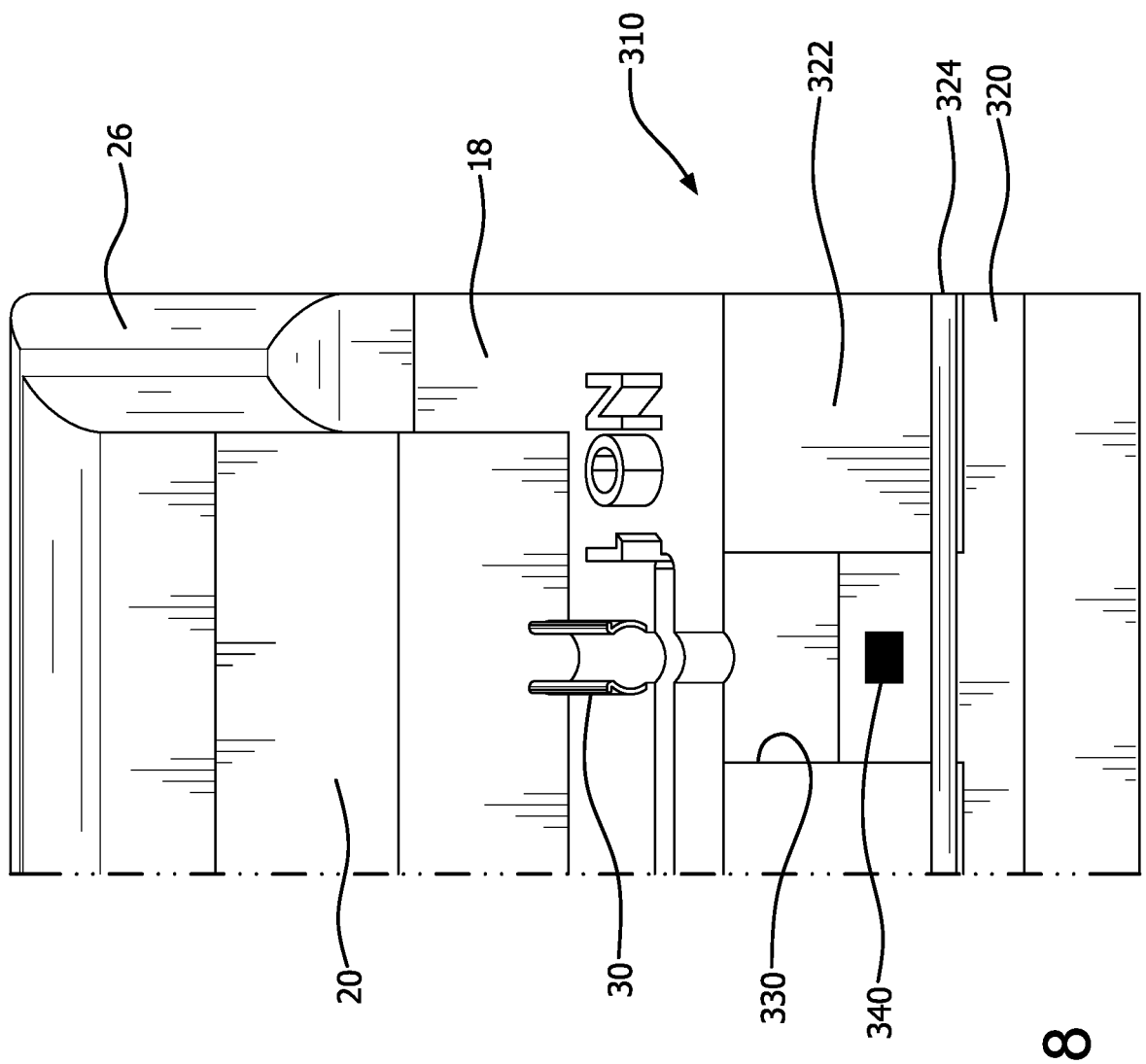
FIG. 8 is another partial top view of the embodiment shown in FIG. 6.
Figure 9:
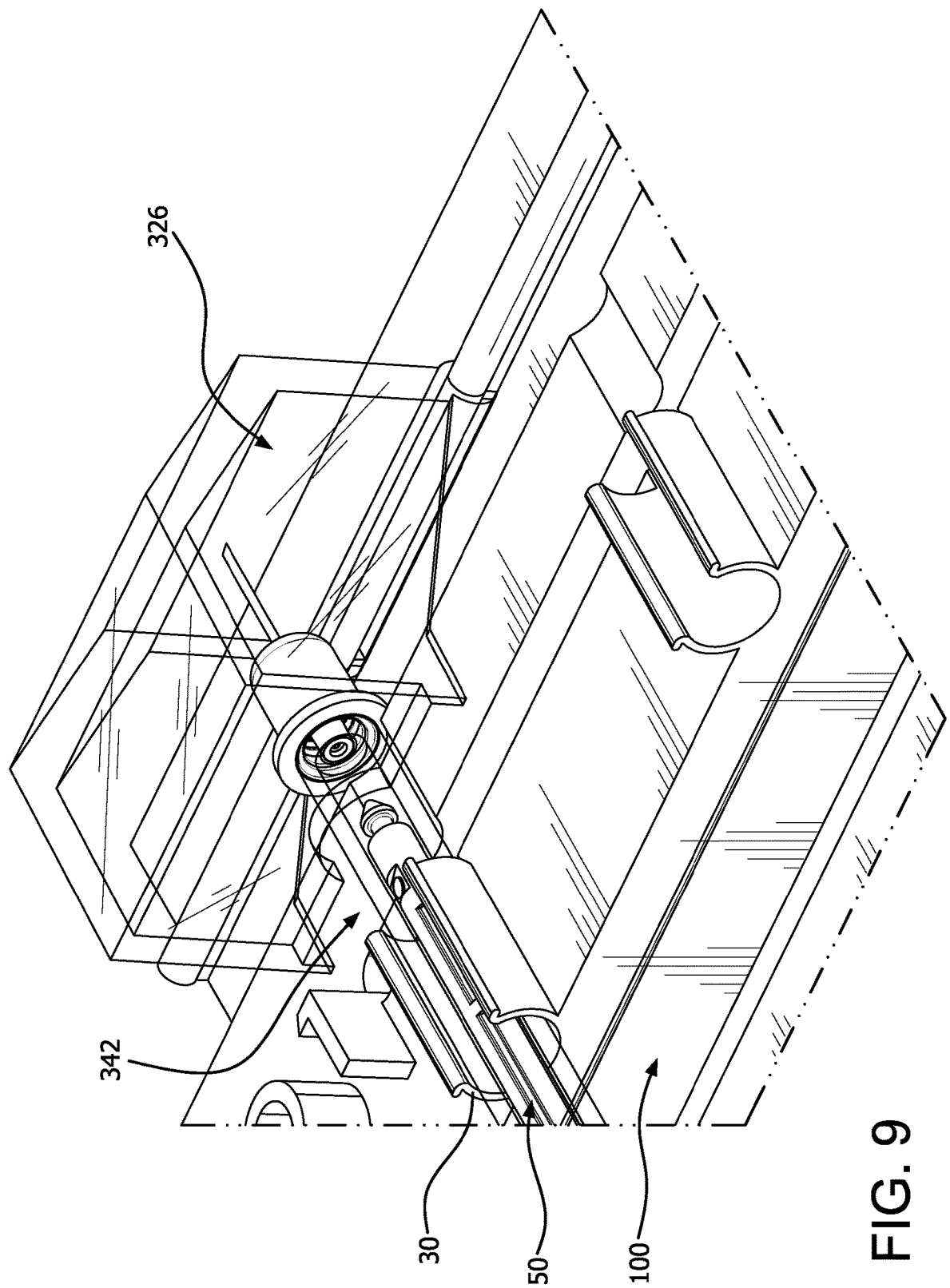
FIG. 9 is another partial top view of the embodiment shown in FIG. 6.

FIG. 7 is a detailed view of the hinged cover 326 as shown in FIG. 6. The hinged cover 326 includes sidewalls 332 that are sloped to match the slope of the ramp 322 and a cutout 334 to accommodate the shape of a barrel of the syringe 50. The same cutout 334 is found in the cover 222 shown in FIG. 5, although the detail is not shown in FIG. 5. The hinged cover 326 rotates on the hinge pin 324 to allow it to be opened and closed as needed. As shown in FIG. 8 each recess 330 also includes an ultraviolet light source 340 to ensure sterility of the area and all things enclosed by the hinged cover 326 when it is in place. As discussed above with respect to tray 210, this UV light source 340 has sufficient power to ensure sterility of the exposed needle and the entire area under the hinged cover 326. The light source 340 would be activated by a switch on the tray 310 or other means for a period of time, such as 30 seconds, to ensure sterility of everything covered by the hinged cover 326. As shown in FIG. 9, there is also a magnetic interface 342 between the hinged cover 326 and the front shelf 18 to ensure that the hinged cover 326 stays closed during transport of the tray 310. The magnetic interface 342 can involve one of the front shelf 18 or the hinged cover 326 being magnetic and the other having a metal portion to ensure a magnetic connection when they are brought into proximity with each other.

One aspect of the present disclosure is to provide a transportation tray to transport filled syringes in a safe manner. The tray includes a front sidewall an opposed rear sidewall and a pair of opposing end walls. The tray preferably has a generally rectangular shape with a front shelf and a rear shelf on the same plane. Located between the front shelf and the rear shelf is a central hole defined by four interior walls. The central hole preferably has a rectangular shape; however, as known by one of skill in the art other shapes could be used. A three-sided raised wall is positioned on top of the two end walls and the rear sidewall. The raised wall extends above the rear shelf. The raised wall includes a pair of end surfaces. The front shelf includes a plurality of sets of paired flexible fingers and a groove located between each of the paired flexible fingers; the sets of paired flexible fingers are spaced apart from each other. In addition, located between each set of paired flexible fingers is an open space. The front shelf further includes optional indicia to serve as an identifying mark to identify each tray. The indicia can use any characters to provide a method of identifying one tray from another. The open spaces serve as a location where a label can be placed to identify the contents of a syringe located in an adjacent set of paired flexible fingers to ensure that the medicament is given to the correct patient and to identify the contents of the syringe.

In another aspect of the present disclosure, the tray further includes a third shelf located adjacent to the front shelf. The third shelf accommodates a cover, which covers a needle of the syringe when the syringe is located in the tray. To secure the cover in place during transport preferably there is a magnetic interface between the cover and the front shelf. Alternatively, the magnetic interface can be located between the cover and the third shelf. An additional feature of the tray is the inclusion of an ultraviolet light source located in the area covered by the cover. This UV light source has sufficient power to ensure sterility of the exposed needle and the entire area under the cover.

In another aspect of the present disclosure, the transportation tray includes a third shelf joined to the front shelf by a ramp. A hinge pin runs the length of the tray where the ramp meets the third shelf; the hinge pin could be segmented as would be known to one of skill in the art. A hinged cover having a hinge that is received on the hinge pin is also included. The hinged cover fits over an exposed needle of a syringe loaded into the tray. An optional UV light source can also be located under the area covered by the cover and used to ensure sterility of the exposed needle and the entire area under the cover Although only a few embodiments of the present invention have been shown and described, the present invention is not limited to the described embodiments. It will be appreciated by those skilled in the art that other changes may also be made to the disclosed embodiments without departing from the scope of the invention. In addition, any of the embodiments, features and/or elements disclosed herein may be combined with one another to form various additional combinations not specifically disclosed, as long as the embodiments, features and/or elements being combined do not contradict each other. All such changes and combinations are considered to be within the scope of the invention as defined by the appended claims and their equivalents.

I claim:

1. A transportation tray to transport filled syringes, the tray comprising:
   a front shelf spaced apart from a rear shelf, with the front shelf and the rear shelf being on approximately the same plane;
   the front shelf including at least one set of paired flexible fingers, the paired flexible fingers spaced being apart sufficiently to accommodate a barrel of a syringe and to thus hold the syringe on the tray;
   a three-sided raised wall adjacent to and extending above the rear shelf; and
   a tray cover, the tray cover being releasably located on the three-sided raised wall.

2. The transportation tray as recited in claim 1, further comprising an arcuate groove located between the paired flexible fingers.

3. The transportation tray as recited in claim 1, wherein each flexible finger of the paired flexible fingers includes a bent back edge.

4. The transportation tray as recited in claim 1, wherein the tray includes a plurality of sets of paired flexible fingers, and at least one of the plurality of sets of paired flexible fingers has a space between its paired flexible fingers that is greater than a space between the paired flexible fingers of another of the plurality of sets of paired flexible fingers.

5. The transportation tray as recited in claim 1, wherein the tray cover is releasably located on the three-sided raised wall by a magnetic interface between the tray cover and the three-sided raised wall.

6. The transportation tray as recited in claim 1 further comprising a third shelf adjacent to the front shelf, the third shelf being lower in height than the front shelf.

7. The transportation tray as recited in claim 6 further comprising at least one cover, the cover being supported on the third shelf.

8. The transportation tray as recited in claim 7 further comprising one of the covers for each of the sets of paired flexible fingers.

9. The transportation tray as recited in claim 7 further comprising a magnetic interface between the tray and the cover to releasably secure the cover to the tray.

10. The transportation tray as recited in claim 7 further comprising an ultraviolet light source adjacent to each set of paired flexible fingers and under the cover when the cover is supported on the third shelf.

11. The transportation tray as recited in claim 10, wherein the ultraviolet light source has sufficient power to sterilize an area under the cover when the cover is supported on the third shelf.

12. A transportation tray to transport filled syringes, the tray comprising:
    a front shelf spaced apart from a rear shelf, with the front shelf and the rear shelf being on approximately the same plane;
    the front shelf including at least one set of paired flexible fingers, the paired flexible fingers spaced being apart sufficiently to accommodate a barrel of a syringe and to thus hold the syringe on the tray;
    a third shelf adjacent to the front shelf, the third shelf being lower in height than the front shelf; and
    a hinge pin located between the front shelf and the third shelf.

13. The transportation tray as recited in claim 12 further comprising at least one cover, the cover having a hinge received on the hinge pin and aligned with one of the pairs of flexible fingers.

14. The transportation tray as recited in claim 13 further comprising one of the covers for each of the sets of paired flexible fingers.

15. The transportation tray as recited in claim 13 further comprising a magnetic interface between the tray and the cover to releasably secure the cover to the tray.

16. The transportation tray as recited in claim 13 further comprising an ultraviolet light source adjacent to each set of paired flexible fingers.

17. The transportation tray as recited in claim 16, wherein the ultraviolet light source has sufficient power to sterilize an area under the cover when the hinge is received on the hinge pin.

18. The transportation tray as recited in claim 14 wherein the tray further comprises a recess associated with each of the paired flexible fingers and wherein the cover is capable of covering the recess.

* * * * *